United States Patent
Lechmann et al.

(10) Patent No.: US 9,463,097 B2
(45) Date of Patent: *Oct. 11, 2016

(54) INTERVERTEBRAL IMPLANT

(71) Applicant: DePuy Synthes Products, Inc., Raynham, MA (US)

(72) Inventors: Beat Lechmann, Zuchwil (CH); Dominique Burkard, Gretzenbach (CH); Christopher Marden John Cain, Aurora, CO (US); Claude Mathieu, Zurich (CH)

(73) Assignee: DePuy Synthes Products, Inc., Raynham, MA (US)

( * ) Notice: Subject to any disclaimer, the term of this patent is extended or adjusted under 35 U.S.C. 154(b) by 284 days.

This patent is subject to a terminal disclaimer.

(21) Appl. No.: 14/273,760

(22) Filed: May 9, 2014

(65) Prior Publication Data

US 2014/0243985 A1 Aug. 28, 2014

Related U.S. Application Data

(63) Continuation of application No. 12/969,330, filed on Dec. 15, 2010, now Pat. No. 8,764,831, which is a
(Continued)

(51) Int. Cl.
*A61F 2/44* (2006.01)
*A61B 17/86* (2006.01)
*A61F 2/30* (2006.01)

(52) U.S. Cl.
CPC ............ *A61F 2/4455* (2013.01); *A61B 17/86* (2013.01); *A61F 2/4465* (2013.01); *A61F 2/442* (2013.01); *A61F 2002/305* (2013.01); *A61F 2002/30383* (2013.01); *A61F 2002/30426* (2013.01); *A61F 2002/30517* (2013.01);
(Continued)

(58) Field of Classification Search
CPC ........ A61F 2/44; A61F 2/4455; A61F 2/446; A61F 2/4465; A61F 2/447; A61F 2002/4475; A61F 2002/448; A61F 2002/4485
See application file for complete search history.

(56) References Cited

U.S. PATENT DOCUMENTS

| 424,836 A | 4/1890 | Thompson |
| 1,105,105 A | 7/1914 | Sherman |

(Continued)

FOREIGN PATENT DOCUMENTS

| AU | 2004/232317 | 11/2010 |
| CA | 2317791 A1 | 8/1999 |

(Continued)

OTHER PUBLICATIONS

U.S. Appl. No. 60/068,205, filed Dec. 19, 1997, Urbahns.
(Continued)

*Primary Examiner* — Lynnsy Summitt
*Assistant Examiner* — Lynnsy Schneider
(74) *Attorney, Agent, or Firm* — Baker & Hostetler LLP

(57) ABSTRACT

An intervertebral implant includes a three-dimensional body and a securing plate. The three-dimensional body includes a front surface and a rear surface. The three-dimensional body further includes a plurality of boreholes for accommodating fixation elements. The intervertebral implant also includes a front plate disposed at the front surface of the three-dimensional body and has a plurality of boreholes. A securing plate can be fastened to the front plate.

31 Claims, 6 Drawing Sheets

Related U.S. Application Data continuation of application No. 12/432,088, filed on Apr. 29, 2009, now Pat. No. 7,862,616, which is a continuation of application No. 11/199,599, filed on Aug. 8, 2005, now Pat. No. 7,846,207, which is a continuation of application No. PCT/CH03/00089, filed on Feb. 6, 2003.

(52) U.S. Cl.
CPC ............... A61F 2002/30593 (2013.01); A61F 2002/30774 (2013.01); A61F 2002/30777 (2013.01); A61F 2002/30843 (2013.01); A61F 2220/0025 (2013.01); A61F 2310/00023 (2013.01)

(56) References Cited

U.S. PATENT DOCUMENTS

| | | |
|---|---|---|
| 1,200,797 A | 10/1916 | Barbe |
| 2,151,919 A | 3/1939 | Jacobson |
| 2,372,888 A | 4/1945 | Edward |
| 2,621,145 A | 12/1952 | Sano |
| 2,782,827 A | 2/1957 | Joseph |
| 2,906,311 A | 9/1959 | Boyd |
| 2,972,367 A | 2/1961 | Wootton |
| 3,062,253 A | 11/1962 | Melvin |
| 3,272,249 A | 9/1966 | Houston |
| 3,350,103 A | 10/1967 | Ahlstone |
| 3,426,364 A | 2/1969 | Lumb et al. |
| 3,561,075 A | 2/1971 | Selinko |
| 3,579,831 A | 5/1971 | Stevens et al. |
| 3,707,303 A | 12/1972 | Petri |
| 3,810,703 A | 5/1974 | Pasbrig |
| 3,867,728 A | 2/1975 | Stubstad et al. |
| 3,899,897 A | 8/1975 | Boerger et al. |
| 3,945,671 A | 3/1976 | Gerlach |
| 4,017,946 A | 4/1977 | Soja |
| 4,056,301 A | 11/1977 | Norden |
| 4,123,132 A | 10/1978 | Hardy |
| 4,135,506 A | 1/1979 | Ulrich |
| 4,278,120 A | 7/1981 | Hart et al. |
| 4,280,875 A | 7/1981 | Werres |
| 4,285,377 A | 8/1981 | Hart |
| 4,288,902 A | 9/1981 | Franz |
| 4,297,063 A | 10/1981 | Hart |
| 4,298,993 A | 11/1981 | Kovaleva et al. |
| 4,299,902 A | 11/1981 | Soma et al. |
| 4,349,921 A | 9/1982 | Kuntz |
| 4,388,921 A | 6/1983 | Sutter et al. |
| 4,394,370 A | 7/1983 | Jefferies |
| 4,450,591 A | 5/1984 | Rappaport |
| 4,484,570 A | 11/1984 | Sutter et al. |
| 4,488,543 A | 12/1984 | Tornier |
| 4,501,269 A | 2/1985 | Bagby |
| 4,503,848 A | 3/1985 | Casper et al. |
| 4,512,038 A | 4/1985 | Alexander et al. |
| 4,545,374 A | 10/1985 | Jacobson |
| 4,553,890 A | 11/1985 | Gulistan |
| 4,599,086 A | 7/1986 | Doty |
| 4,627,853 A | 12/1986 | Campbell et al. |
| 4,640,524 A | 2/1987 | Sedlmair |
| 4,648,768 A | 3/1987 | Hambric |
| 4,678,470 A | 7/1987 | Nashef et al. |
| 4,708,377 A | 11/1987 | Hunting |
| 4,711,760 A | 12/1987 | Blaushild |
| 4,714,469 A | 12/1987 | Kenna |
| 4,717,115 A | 1/1988 | Schmitz et al. |
| 4,743,256 A | 5/1988 | Brantigan |
| 4,781,721 A | 11/1988 | Grundei |
| 4,793,335 A | 12/1988 | Frey et al. |
| 4,804,290 A | 2/1989 | Balsells |
| 4,812,094 A | 3/1989 | Grube |
| 4,829,152 A | 5/1989 | Rostoker et al. |
| 4,834,757 A | 5/1989 | Brantigan |
| 4,858,603 A | 8/1989 | Clemow et al. |
| 4,872,452 A | 10/1989 | Alexson |
| 4,878,915 A | 11/1989 | Brantigan |
| 4,904,261 A | 2/1990 | Dove et al. |
| 4,917,704 A | 4/1990 | Frey et al. |
| 4,936,851 A | 6/1990 | Fox et al. |
| 4,950,296 A | 8/1990 | McIntyre |
| 4,955,908 A | 9/1990 | Frey et al. |
| 4,961,740 A | 10/1990 | Ray et al. |
| 4,976,576 A | 12/1990 | Mahaney |
| 4,978,350 A | 12/1990 | Wagenknecht |
| 4,994,084 A | 2/1991 | Brennan |
| 4,997,432 A | 3/1991 | Keller |
| 5,006,120 A | 4/1991 | Carter |
| 5,010,783 A | 4/1991 | Sparks et al. |
| 5,017,069 A | 5/1991 | Stencel |
| 5,020,949 A | 6/1991 | Davidson et al. |
| 5,026,373 A | 6/1991 | Ray et al. |
| 5,030,220 A | 7/1991 | Howland |
| 5,047,058 A | 9/1991 | Roberts et al. |
| 5,053,049 A | 10/1991 | Campbell |
| 5,062,850 A | 11/1991 | MacMillan et al. |
| 5,071,437 A | 12/1991 | Steffee |
| 5,084,051 A | 1/1992 | Tormala et al. |
| 5,085,660 A | 2/1992 | Lin |
| 5,096,150 A | 3/1992 | Westwood |
| 5,108,438 A | 4/1992 | Stone et al. |
| 5,112,354 A | 5/1992 | Sires |
| 5,116,374 A | 5/1992 | Stone |
| 5,118,235 A | 6/1992 | Dill |
| 5,139,424 A | 8/1992 | Yli-Urpo |
| 5,147,404 A | 9/1992 | Downey |
| 5,180,381 A | 1/1993 | Aust et al. |
| 5,192,327 A | 3/1993 | Brantigan |
| 5,201,736 A | 4/1993 | Strauss |
| 5,207,543 A | 5/1993 | Kirma |
| 5,211,664 A | 5/1993 | Tepic et al. |
| 5,235,034 A | 8/1993 | Bobsein et al. |
| 5,238,342 A | 8/1993 | Stencel |
| 5,258,031 A | 11/1993 | Salib et al. |
| 5,275,601 A | 1/1994 | Gogolewski et al. |
| 5,281,226 A | 1/1994 | Davydov et al. |
| 5,282,861 A | 2/1994 | Kaplan |
| 5,284,655 A | 2/1994 | Bogdansky et al. |
| 5,290,312 A | 3/1994 | Kojimoto et al. |
| 5,298,254 A | 3/1994 | Prewett et al. |
| 5,304,021 A | 4/1994 | Oliver et al. |
| 5,306,308 A | 4/1994 | Gross et al. |
| 5,306,309 A | 4/1994 | Wagner et al. |
| 5,314,476 A | 5/1994 | Prewett et al. |
| 5,314,477 A | 5/1994 | Marnay |
| 5,330,535 A | 7/1994 | Moser et al. |
| 5,348,788 A | 9/1994 | White |
| 5,368,593 A | 11/1994 | Stark |
| 5,380,323 A | 1/1995 | Howland |
| 5,385,583 A | 1/1995 | Cotrel |
| 5,397,364 A * | 3/1995 | Kozak ............... A61B 17/025 606/247 |
| 5,405,391 A | 4/1995 | Hednerson et al. |
| 5,411,348 A | 5/1995 | Balsells |
| 5,423,817 A | 6/1995 | Lin |
| 5,425,772 A | 6/1995 | Brantigan |
| 5,431,658 A | 7/1995 | Moskovich |
| 5,439,684 A | 8/1995 | Prewett et al. |
| 5,443,514 A | 8/1995 | Steffee |
| 5,443,515 A | 8/1995 | Cohen et al. |
| 5,458,638 A | 10/1995 | Kuslich et al. |
| 5,458,641 A | 10/1995 | Ramirez |
| 5,458,643 A | 10/1995 | Oka et al. |
| 5,478,342 A | 12/1995 | Kohrs |
| 5,484,437 A | 1/1996 | Michelson |
| 5,487,744 A | 1/1996 | Howland |
| 5,489,308 A | 2/1996 | Kuslich et al. |
| 5,507,818 A | 4/1996 | McLaughlin |
| 5,514,180 A | 5/1996 | Heggeness et al. |
| 5,520,690 A | 5/1996 | Errico et al. |
| 5,522,899 A | 6/1996 | Michelson |
| 5,531,746 A | 7/1996 | Errico et al. |
| 5,534,030 A | 7/1996 | Navarro et al. |
| 5,534,031 A | 7/1996 | Matsuzaki et al. |

(56) References Cited

U.S. PATENT DOCUMENTS

| | | |
|---|---|---|
| 5,534,032 A | 7/1996 | Hodorek |
| 5,545,842 A | 8/1996 | Balsells |
| 5,549,612 A | 8/1996 | Yapp et al. |
| 5,549,679 A | 8/1996 | Kuslich |
| 5,550,172 A | 8/1996 | Regula et al. |
| 5,554,191 A | 9/1996 | Lahille et al. |
| 5,556,430 A | 9/1996 | Gendler |
| 5,556,431 A | 9/1996 | Buttner-Janz |
| 5,569,308 A | 10/1996 | Sottosanti |
| 5,570,983 A | 11/1996 | Hollander |
| 5,571,190 A | 11/1996 | Ulrich et al. |
| 5,571,192 A | 11/1996 | Schonhoffer |
| 5,578,034 A | 11/1996 | Estes |
| 5,593,409 A | 1/1997 | Michelson |
| 5,597,278 A | 1/1997 | Peterkort |
| 5,601,553 A | 2/1997 | Trebing et al. |
| 5,601,554 A | 2/1997 | Howland et al. |
| 5,607,428 A | 3/1997 | Lin |
| 5,607,474 A | 3/1997 | Athanasiou et al. |
| 5,609,635 A | 3/1997 | Michelson |
| 5,609,636 A | 3/1997 | Kohrs et al. |
| 5,609,637 A | 3/1997 | Biedermann et al. |
| 5,616,144 A | 4/1997 | Yapp et al. |
| 5,620,448 A | 4/1997 | Puddu |
| 5,642,960 A | 7/1997 | Salice |
| 5,645,596 A | 7/1997 | Kim et al. |
| 5,645,606 A | 7/1997 | Oehy et al. |
| 5,653,708 A | 8/1997 | Howland |
| 5,669,909 A | 9/1997 | Zdeblick et al. |
| 5,674,296 A | 10/1997 | Bryan et al. |
| 5,676,666 A | 10/1997 | Oxland |
| 5,676,699 A | 10/1997 | Gogolewski |
| 5,681,311 A | 10/1997 | Foley et al. |
| 5,683,216 A | 11/1997 | Erbes |
| 5,683,394 A | 11/1997 | Rinner |
| 5,683,463 A | 11/1997 | Godefroy et al. |
| 5,702,449 A | 12/1997 | Mckay |
| 5,702,451 A | 12/1997 | Biedermann et al. |
| 5,702,453 A | 12/1997 | Rabbe et al. |
| 5,702,455 A | 12/1997 | Saggar |
| 5,713,899 A | 2/1998 | Marnay et al. |
| 5,713,900 A | 2/1998 | Benzel et al. |
| 5,725,531 A | 3/1998 | Shapiro |
| 5,725,588 A | 3/1998 | Errico et al. |
| 5,728,159 A | 3/1998 | Stroever et al. |
| 5,735,853 A | 4/1998 | Olerud |
| 5,735,905 A | 4/1998 | Parr |
| 5,755,796 A | 5/1998 | Ibo et al. |
| 5,755,798 A | 5/1998 | Papavero et al. |
| 5,766,251 A | 6/1998 | Koshino |
| 5,766,252 A | 6/1998 | Henry et al. |
| 5,766,253 A | 6/1998 | Brosnahan, III |
| 5,772,661 A | 6/1998 | Michelson |
| 5,776,194 A | 7/1998 | Mikol et al. |
| 5,776,196 A | 7/1998 | Matsuzaki et al. |
| 5,776,197 A | 7/1998 | Rabbe et al. |
| 5,776,198 A | 7/1998 | Rabbe et al. |
| 5,776,199 A | 7/1998 | Michelson |
| 5,778,804 A | 7/1998 | Read |
| 5,782,915 A | 7/1998 | Stone |
| 5,782,919 A | 7/1998 | Zdeblick et al. |
| 5,785,710 A | 7/1998 | Michelson |
| 5,800,433 A | 9/1998 | Benzel et al. |
| 5,836,948 A | 11/1998 | Zucherman et al. |
| 5,860,973 A | 1/1999 | Michelson |
| 5,861,041 A | 1/1999 | Tienboon |
| 5,865,845 A | 2/1999 | Thalgott |
| 5,865,849 A | 2/1999 | Stone |
| 5,876,402 A | 3/1999 | Errico et al. |
| 5,876,452 A | 3/1999 | Athanasiou et al. |
| 5,879,389 A | 3/1999 | Koshino |
| 5,885,299 A | 3/1999 | Winslow et al. |
| 5,888,222 A | 3/1999 | Coates et al. |
| 5,888,223 A | 3/1999 | Bray, Jr. |
| 5,888,224 A | 3/1999 | Beckers et al. |
| 5,888,227 A | 3/1999 | Cottle |
| 5,895,426 A | 4/1999 | Scarborough et al. |
| 5,899,939 A | 5/1999 | Boyce et al. |
| 5,902,303 A | 5/1999 | Eckhof et al. |
| 5,902,338 A | 5/1999 | Stone |
| 5,904,683 A | 5/1999 | Pohndorf et al. |
| 5,904,719 A | 5/1999 | Errico et al. |
| 5,906,616 A | 5/1999 | Pavlov et al. |
| 5,910,315 A | 6/1999 | Stevenson et al. |
| 5,911,758 A | 6/1999 | Oehy et al. |
| 5,920,312 A | 7/1999 | Wagner et al. |
| 5,922,027 A | 7/1999 | Stone |
| 5,931,838 A | 8/1999 | Vito |
| 5,944,755 A | 8/1999 | Stone |
| 5,951,558 A | 9/1999 | Fiz |
| 5,954,722 A | 9/1999 | Bono |
| 5,958,314 A | 9/1999 | Draenet |
| 5,964,807 A | 10/1999 | Gan et al. |
| 5,968,098 A | 10/1999 | Winslow |
| 5,972,368 A | 10/1999 | McKay |
| 5,976,141 A | 11/1999 | Haag et al. |
| 5,976,187 A | 11/1999 | Richelsoph |
| 5,980,522 A | 11/1999 | Koros et al. |
| 5,981,828 A | 11/1999 | Nelson et al. |
| 5,984,967 A | 11/1999 | Zdeblick et al. |
| 5,989,289 A | 11/1999 | Coates et al. |
| 6,001,099 A | 12/1999 | Huebner |
| 6,008,433 A | 12/1999 | Stone |
| 6,013,853 A | 1/2000 | Athanasiou et al. |
| 6,017,345 A | 1/2000 | Richelsoph |
| 6,025,538 A | 2/2000 | Yaccarino, III |
| 6,033,405 A | 3/2000 | Winslow et al. |
| 6,033,438 A | 3/2000 | Bianchi et al. |
| 6,039,762 A | 3/2000 | McKay |
| 6,045,579 A | 4/2000 | Hochshuler et al. |
| 6,045,580 A | 4/2000 | Scarborough et al. |
| 6,056,749 A | 5/2000 | Kuslich |
| 6,066,175 A | 5/2000 | Henderson et al. |
| 6,080,158 A | 6/2000 | Lin |
| 6,080,193 A | 6/2000 | Hochshuler et al. |
| 6,086,593 A | 7/2000 | Bonutti |
| 6,086,614 A | 7/2000 | Mumme |
| 6,090,998 A | 7/2000 | Grooms et al. |
| 6,096,080 A | 8/2000 | Nicholson et al. |
| 6,096,081 A | 8/2000 | Grivas et al. |
| 6,099,531 A | 8/2000 | Bonutti |
| 6,110,482 A | 8/2000 | Khouri et al. |
| 6,113,637 A | 9/2000 | Gill et al. |
| 6,113,638 A | 9/2000 | Williams et al. |
| 6,120,503 A | 9/2000 | Michelson |
| 6,123,731 A | 9/2000 | Boyce et al. |
| 6,129,763 A | 10/2000 | Chauvin et al. |
| 6,136,001 A | 10/2000 | Michelson |
| 6,139,550 A | 10/2000 | Michelson |
| 6,143,030 A | 11/2000 | Schroder |
| 6,143,033 A | 11/2000 | Paul et al. |
| 6,146,421 A | 11/2000 | Gordon et al. |
| 6,156,070 A | 12/2000 | Incavo et al. |
| 6,193,721 B1 | 2/2001 | Michelson |
| 6,193,756 B1 | 2/2001 | Studer et al. |
| 6,193,757 B1 | 2/2001 | Foley et al. |
| 6,200,347 B1 | 3/2001 | Anderson et al. |
| 6,206,922 B1 | 3/2001 | Zdeblick et al. |
| 6,224,602 B1 | 5/2001 | Hayes |
| 6,231,610 B1 | 5/2001 | Geisler |
| 6,235,033 B1 | 5/2001 | Brace et al. |
| 6,235,034 B1 | 5/2001 | Bray |
| 6,235,059 B1 | 5/2001 | Benezech et al. |
| 6,241,731 B1 | 6/2001 | Fiz |
| 6,241,769 B1 | 6/2001 | Nicholson et al. |
| 6,245,108 B1 | 6/2001 | Biscup |
| 6,258,089 B1 | 7/2001 | Campbell et al. |
| 6,258,125 B1 | 7/2001 | Paul et al. |
| 6,261,291 B1 | 7/2001 | Talaber et al. |
| 6,261,586 B1 | 7/2001 | McKay |
| 6,264,695 B1 | 7/2001 | Stoy |
| 6,270,528 B1 | 8/2001 | McKay |
| 6,306,139 B1 | 10/2001 | Fuentes |
| 6,322,562 B1 | 11/2001 | Wolter |

(56) References Cited

U.S. PATENT DOCUMENTS

| | | |
|---|---|---|
| 6,331,179 B1 | 12/2001 | Freid et al. |
| 6,342,074 B1 | 1/2002 | Simpson |
| 6,364,880 B1 | 4/2002 | Michelson |
| 6,371,986 B1 | 4/2002 | Bagby |
| 6,371,988 B1 | 4/2002 | Pafford et al. |
| 6,371,989 B1 | 4/2002 | Chauvin et al. |
| 6,375,681 B1 | 4/2002 | Truscott |
| 6,383,186 B1 | 5/2002 | Michelson |
| 6,387,130 B1 | 5/2002 | Stone et al. |
| 6,395,031 B1 | 5/2002 | Foley et al. |
| 6,398,811 B1 | 6/2002 | McKay |
| 6,413,259 B1 | 7/2002 | Lyons et al. |
| 6,423,063 B1 | 7/2002 | Bonutti |
| 6,432,106 B1 | 8/2002 | Fraser |
| 6,443,987 B1 | 9/2002 | Bryan |
| 6,447,512 B1 | 9/2002 | Landry et al. |
| 6,447,546 B1 | 9/2002 | Bramlet et al. |
| 6,454,771 B1 | 9/2002 | Michelson |
| 6,458,158 B1 | 10/2002 | Anderson et al. |
| 6,461,359 B1 | 10/2002 | Tribus et al. |
| 6,468,311 B2 | 10/2002 | Boyd et al. |
| 6,471,724 B2 | 10/2002 | Zdeblick et al. |
| 6,482,233 B1 | 11/2002 | Aebi et al. |
| 6,503,250 B2 | 1/2003 | Paul |
| 6,511,509 B1 | 1/2003 | Ford et al. |
| 6,524,312 B2 | 2/2003 | Landry et al. |
| 6,558,387 B2 | 5/2003 | Errico et al. |
| 6,558,423 B1 | 5/2003 | Michelson |
| 6,558,424 B2 | 5/2003 | Thalgott |
| 6,562,073 B2 | 5/2003 | Foley |
| 6,569,201 B2 | 5/2003 | Moumene et al. |
| 6,575,975 B2 | 6/2003 | Brace et al. |
| 6,576,017 B2 | 6/2003 | Foley et al. |
| 6,579,290 B1 | 6/2003 | Hardcastle et al. |
| 6,592,624 B1 | 7/2003 | Fraser et al. |
| 6,602,291 B1 | 8/2003 | Ray et al. |
| 6,605,090 B1 | 8/2003 | Trieu et al. |
| 6,616,671 B2 | 9/2003 | Landry et al. |
| 6,620,163 B1 | 9/2003 | Michelson |
| 6,623,486 B1 | 9/2003 | Weaver et al. |
| 6,629,998 B1 | 10/2003 | Lin |
| 6,638,310 B2 | 10/2003 | Lin et al. |
| 6,645,212 B2 | 11/2003 | Goldhahn et al. |
| 6,652,525 B1 | 11/2003 | Assaker et al. |
| 6,656,181 B2 | 12/2003 | Dixon et al. |
| 6,679,887 B2 | 1/2004 | Nicholson et al. |
| 6,682,561 B2 | 1/2004 | Songer et al. |
| 6,682,563 B2 | 1/2004 | Scharf |
| 6,695,846 B2 | 2/2004 | Richelsoph et al. |
| 6,695,851 B2 | 2/2004 | Zdeblick et al. |
| 6,706,067 B2 | 3/2004 | Shimp et al. |
| 6,709,456 B2 | 3/2004 | Langberg et al. |
| 6,712,818 B1 | 3/2004 | Michelson |
| 6,730,127 B2 | 5/2004 | Michelson |
| 6,736,850 B2 | 5/2004 | Davis |
| 6,761,739 B2 | 7/2004 | Shepard |
| 6,770,096 B2 | 8/2004 | Bolger et al. |
| 6,786,909 B1 | 9/2004 | Dransfeld et al. |
| 6,800,092 B1 | 10/2004 | Williams et al. |
| 6,805,714 B2 | 10/2004 | Sutcliffe |
| 6,808,537 B2 | 10/2004 | Michelson |
| 6,824,564 B2 | 11/2004 | Crozet |
| 6,833,006 B2 | 12/2004 | Foley et al. |
| 6,837,905 B1 | 1/2005 | Lieberman |
| 6,849,093 B2 | 2/2005 | Michelson |
| 6,855,168 B2 | 2/2005 | Crozet |
| 6,863,673 B2 | 3/2005 | Gerbec et al. |
| 6,872,915 B2 | 3/2005 | Koga et al. |
| 6,884,242 B2 | 4/2005 | LeHuec et al. |
| 6,890,334 B2 | 5/2005 | Brace et al. |
| 6,896,701 B2 | 5/2005 | Boyd et al. |
| 6,899,735 B2 | 5/2005 | Coates et al. |
| 6,902,578 B1 | 6/2005 | Anderson et al. |
| 6,916,320 B2 | 7/2005 | Michelson |
| 6,923,756 B2 | 8/2005 | Sudakov et al. |
| 6,953,477 B2 | 10/2005 | Berry |
| 6,962,606 B2 | 11/2005 | Michelson |
| 6,964,664 B2 | 11/2005 | Freid et al. |
| 6,964,687 B1 | 11/2005 | Bernard et al. |
| 6,972,019 B2 * | 12/2005 | Michelson ............ A61F 2/4611 606/247 |
| 6,972,035 B2 | 12/2005 | Michelson |
| 6,974,479 B2 | 12/2005 | Trieu |
| 6,984,234 B2 | 1/2006 | Bray |
| 7,001,385 B2 | 2/2006 | Bonutti |
| 7,001,432 B2 | 2/2006 | Keller et al. |
| 7,018,416 B2 | 3/2006 | Hanson et al. |
| 7,033,394 B2 | 4/2006 | Michelson |
| 7,041,135 B2 | 5/2006 | Michelson |
| 7,044,968 B1 | 5/2006 | Yaccarino et al. |
| 7,044,972 B2 | 5/2006 | Mathys et al. |
| 7,048,765 B1 | 5/2006 | Grooms et al. |
| 7,060,097 B2 | 6/2006 | Fraser et al. |
| 7,066,961 B2 | 6/2006 | Michelson |
| 7,077,864 B2 | 7/2006 | Byrd, III et al. |
| 7,112,222 B2 | 9/2006 | Fraser et al. |
| 7,112,223 B2 | 9/2006 | Davis |
| 7,135,024 B2 | 11/2006 | Cook et al. |
| 7,135,043 B2 | 11/2006 | Nakahara et al. |
| 7,137,984 B2 | 11/2006 | Michelson |
| 7,147,665 B1 | 12/2006 | Bryan et al. |
| 7,163,561 B2 | 1/2007 | Michelson |
| 7,172,627 B2 | 2/2007 | Fiere et al. |
| 7,172,672 B2 | 2/2007 | Silverbrook |
| 7,226,452 B2 | 6/2007 | Zubok |
| 7,226,482 B2 | 6/2007 | Messerli et al. |
| 7,232,463 B2 | 6/2007 | Falahee |
| 7,232,464 B2 | 6/2007 | Mathieu et al. |
| 7,238,203 B2 | 7/2007 | Bagga et al. |
| 7,255,698 B2 | 8/2007 | Michelson |
| 7,276,082 B2 | 10/2007 | Zdeblick et al. |
| 7,320,708 B1 | 1/2008 | Bernstein |
| 7,323,011 B2 | 1/2008 | Shepard et al. |
| 7,442,209 B2 | 10/2008 | Michelson |
| 7,491,237 B2 | 2/2009 | Randall et al. |
| 7,534,265 B1 | 5/2009 | Boyd et al. |
| 7,594,932 B2 | 9/2009 | Aferzon et al. |
| 7,601,173 B2 | 10/2009 | Messerli et al. |
| 7,608,107 B2 | 10/2009 | Michelson |
| 7,618,456 B2 | 11/2009 | Mathieu et al. |
| 7,621,960 B2 | 11/2009 | Boyd et al. |
| 7,625,380 B2 | 12/2009 | Drewry et al. |
| 7,637,951 B2 | 12/2009 | Michelson |
| 7,655,042 B2 | 2/2010 | Foley et al. |
| 7,704,279 B2 | 4/2010 | Moskowitz et al. |
| 7,846,188 B2 | 12/2010 | Moskowitz et al. |
| 7,846,207 B2 | 12/2010 | Lechmann et al. |
| 7,862,616 B2 | 1/2011 | Lechmann |
| 7,875,076 B2 | 1/2011 | Mathieu et al. |
| 7,942,903 B2 | 5/2011 | Moskowitz et al. |
| 7,993,403 B2 | 8/2011 | Foley et al. |
| 8,062,303 B2 | 11/2011 | Berry et al. |
| 8,128,700 B2 | 3/2012 | Delurio et al. |
| 8,182,532 B2 | 5/2012 | Anderson et al. |
| 8,211,148 B2 | 7/2012 | Zhang et al. |
| 8,273,127 B2 | 9/2012 | Jones et al. |
| 8,308,804 B2 | 11/2012 | Krueger |
| 8,328,872 B2 | 12/2012 | Duffield et al. |
| 8,343,222 B2 | 1/2013 | Cope |
| 8,353,913 B2 | 1/2013 | Moskowitz et al. |
| 8,382,768 B2 | 2/2013 | Berry et al. |
| 8,425,607 B2 | 4/2013 | Waugh et al. |
| 8,444,696 B2 | 5/2013 | Michelson |
| 8,465,546 B2 | 6/2013 | Jodaitis et al. |
| 8,540,774 B2 | 9/2013 | Kueenzi et al. |
| 8,545,567 B1 | 10/2013 | Krueger |
| 8,641,743 B2 | 2/2014 | Michelson |
| 8,641,768 B2 | 2/2014 | Duffield et al. |
| 8,764,831 B2 | 7/2014 | Lechmann et al. |
| 9,005,295 B2 | 4/2015 | Kueenzi et al. |
| 2001/0001129 A1 | 5/2001 | McKay et al. |
| 2001/0005796 A1 | 6/2001 | Zdeblick et al. |
| 2001/0010021 A1 | 7/2001 | Boyd et al. |
| 2001/0016777 A1 | 8/2001 | Biscup |

(56) References Cited

U.S. PATENT DOCUMENTS

| | | |
|---|---|---|
| 2001/0020186 A1 | 9/2001 | Boyee et al. |
| 2001/0031254 A1 | 10/2001 | Bianchi et al. |
| 2001/0039456 A1 | 11/2001 | Boyer, II et al. |
| 2001/0041941 A1 | 11/2001 | Boyer, II et al. |
| 2002/0004683 A1 | 1/2002 | Michelson et al. |
| 2002/0010511 A1 | 1/2002 | Michelson |
| 2002/0016595 A1 | 2/2002 | Michelson |
| 2002/0022843 A1 | 2/2002 | Michelson |
| 2002/0029084 A1 | 3/2002 | Paul et al. |
| 2002/0065517 A1 | 5/2002 | Paul |
| 2002/0082597 A1 | 6/2002 | Fraser |
| 2002/0082603 A1 | 6/2002 | Dixon et al. |
| 2002/0091447 A1 | 7/2002 | Shimp et al. |
| 2002/0095155 A1 | 7/2002 | Michelson |
| 2002/0099376 A1 | 7/2002 | Michelson |
| 2002/0099378 A1 | 7/2002 | Michelson |
| 2002/0106393 A1 | 8/2002 | Bianchi et al. |
| 2002/0111680 A1 | 8/2002 | Michelson |
| 2002/0128712 A1 | 9/2002 | Michelson |
| 2002/0128717 A1 | 9/2002 | Alfaro et al. |
| 2002/0147450 A1 | 10/2002 | LeHuec et al. |
| 2002/0169508 A1 | 11/2002 | Songer et al. |
| 2002/0193880 A1 | 12/2002 | Fraser |
| 2003/0045939 A1 | 3/2003 | Casutt |
| 2003/0078668 A1 | 4/2003 | Michelson |
| 2003/0125739 A1 | 7/2003 | Bagga et al. |
| 2003/0135277 A1 | 7/2003 | Bryan et al. |
| 2003/0153975 A1 | 8/2003 | Byrd |
| 2003/0167092 A1 | 9/2003 | Foley |
| 2003/0195626 A1 | 10/2003 | Huppert |
| 2003/0195632 A1 | 10/2003 | Foley et al. |
| 2003/0199881 A1 | 10/2003 | Bonutti |
| 2003/0199983 A1 | 10/2003 | Michelson |
| 2004/0078078 A1 | 4/2004 | Shepard |
| 2004/0078081 A1 | 4/2004 | Ferree |
| 2004/0092929 A1 | 5/2004 | Zindrick |
| 2004/0093084 A1 | 5/2004 | Michelson |
| 2004/0102848 A1 | 5/2004 | Michelson |
| 2004/0126407 A1 | 7/2004 | Falahee |
| 2004/0133278 A1 | 7/2004 | Marino et al. |
| 2004/0143270 A1 | 7/2004 | Zucherman et al. |
| 2004/0176853 A1 | 9/2004 | Sennett et al. |
| 2004/0199254 A1 | 10/2004 | Louis et al. |
| 2004/0210219 A1 | 10/2004 | Bray |
| 2004/0210310 A1 | 10/2004 | Trieu |
| 2004/0210314 A1 | 10/2004 | Michelson |
| 2004/0249377 A1 | 12/2004 | Kaes et al. |
| 2004/0254644 A1 | 12/2004 | Taylor |
| 2005/0015149 A1 | 1/2005 | Michelson |
| 2005/0021143 A1 | 1/2005 | Keller |
| 2005/0033433 A1 | 2/2005 | Michelson |
| 2005/0049593 A1 | 3/2005 | Duong et al. |
| 2005/0049595 A1 | 3/2005 | Suh et al. |
| 2005/0065605 A1 | 3/2005 | Jackson |
| 2005/0065607 A1 | 3/2005 | Gross |
| 2005/0065608 A1 | 3/2005 | Michelson |
| 2005/0071008 A1 | 3/2005 | Kirschman |
| 2005/0085913 A1 | 4/2005 | Fraser et al. |
| 2005/0101960 A1 | 5/2005 | Fiere et al. |
| 2005/0149193 A1 | 7/2005 | Zucherman et al. |
| 2005/0154391 A1 | 7/2005 | Doherty et al. |
| 2005/0159813 A1 | 7/2005 | Molz |
| 2005/0159818 A1 | 7/2005 | Blain |
| 2005/0159819 A1 | 7/2005 | McCormick et al. |
| 2005/0171607 A1 | 8/2005 | Michelson |
| 2005/0177236 A1 | 8/2005 | Mathieu et al. |
| 2005/0240267 A1 | 10/2005 | Randall et al. |
| 2005/0240271 A1 | 10/2005 | Zubok et al. |
| 2005/0261767 A1 | 11/2005 | Anderson et al. |
| 2006/0020342 A1 | 1/2006 | Feree et al. |
| 2006/0030851 A1 | 2/2006 | Bray et al. |
| 2006/0079901 A1 | 4/2006 | Ryan et al. |
| 2006/0079961 A1 | 4/2006 | Michelson |
| 2006/0085071 A1 | 4/2006 | Lechmann et al. |
| 2006/0089717 A1 | 4/2006 | Krishna |
| 2006/0129240 A1 | 6/2006 | Lessar et al. |
| 2006/0136063 A1 | 6/2006 | Zeegers |
| 2006/0142765 A9 | 6/2006 | Dixon et al. |
| 2006/0195189 A1 | 8/2006 | Link et al. |
| 2006/0206208 A1 | 9/2006 | Michelson |
| 2006/0229725 A1 | 10/2006 | Lechmann et al. |
| 2007/0088441 A1 | 4/2007 | Duggal et al. |
| 2007/0093819 A1 | 4/2007 | Albert |
| 2007/0106384 A1 | 5/2007 | Bray et al. |
| 2007/0118125 A1 | 5/2007 | Orbay et al. |
| 2007/0123987 A1 | 5/2007 | Bernstein |
| 2007/0162130 A1 | 7/2007 | Rashbaum et al. |
| 2007/0168032 A1 | 7/2007 | Muhanna et al. |
| 2007/0219635 A1 | 9/2007 | Mathieu et al. |
| 2007/0225806 A1 | 9/2007 | Squires et al. |
| 2007/0225812 A1 | 9/2007 | Gill |
| 2007/0250167 A1 | 10/2007 | Bray et al. |
| 2007/0270961 A1 | 11/2007 | Ferguson |
| 2008/0033440 A1 | 2/2008 | Moskowitz et al. |
| 2008/0051890 A1 | 2/2008 | Waugh et al. |
| 2008/0082169 A1 | 4/2008 | Gittings |
| 2008/0119933 A1 | 5/2008 | Aebi et al. |
| 2008/0133013 A1 | 6/2008 | Duggal et al. |
| 2008/0161925 A1 | 7/2008 | Brittan et al. |
| 2008/0177307 A1 | 7/2008 | Moskowitz et al. |
| 2008/0200984 A1 | 8/2008 | Jodaitis et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0269806 A1 | 10/2008 | Zhang et al. |
| 2008/0275455 A1 | 11/2008 | Berry et al. |
| 2008/0306596 A1 | 12/2008 | Jones et al. |
| 2009/0076608 A1 | 3/2009 | Gordon et al. |
| 2009/0105830 A1 | 4/2009 | Jones et al. |
| 2009/0192613 A1 | 7/2009 | Wing et al. |
| 2009/0210062 A1 | 8/2009 | Thalgott et al. |
| 2009/0210064 A1 | 8/2009 | Lechmann et al. |
| 2009/0234455 A1 | 9/2009 | Moskowitz et al. |
| 2009/0326580 A1 | 12/2009 | Anderson et al. |
| 2010/0016901 A1 | 1/2010 | Robinson |
| 2010/0125334 A1 | 5/2010 | Krueger |
| 2010/0145459 A1 | 6/2010 | McDonough et al. |
| 2010/0145460 A1 | 6/2010 | McDonough et al. |
| 2011/0118843 A1 | 5/2011 | Mathieu et al. |
| 2011/0295371 A1 | 12/2011 | Moskowitz et al. |
| 2012/0101581 A1 | 4/2012 | Mathieu et al. |
| 2012/0109309 A1 | 5/2012 | Mathieu et al. |
| 2012/0109310 A1 | 5/2012 | Mathieu et al. |
| 2012/0109311 A1 | 5/2012 | Mathieu et al. |
| 2012/0109312 A1 | 5/2012 | Mathieu et al. |
| 2012/0109313 A1 | 5/2012 | Mathieu et al. |
| 2012/0179259 A1 | 7/2012 | McDonough et al. |
| 2013/0073046 A1 | 3/2013 | Zaveloff et al. |
| 2013/0073047 A1 | 3/2013 | Laskowitz et al. |
| 2013/0166032 A1 | 6/2013 | McDonough et al. |
| 2013/0173013 A1 | 7/2013 | Anderson et al. |
| 2013/0268008 A1 | 10/2013 | McDonough et al. |
| 2014/0025168 A1 | 1/2014 | Klimek et al. |
| 2014/0121777 A1 | 5/2014 | Rosen et al. |
| 2014/0180422 A1 | 6/2014 | Klimek et al. |
| 2014/0257487 A1 | 9/2014 | Lawson et al. |
| 2014/0336770 A1 | 11/2014 | Petersheim et al. |
| 2014/0371859 A1 | 12/2014 | Petersheim et al. |

FOREIGN PATENT DOCUMENTS

| | | |
|---|---|---|
| DE | 2821678 A | 11/1979 |
| DE | 3042003 A1 | 7/1982 |
| DE | 3933459 A1 | 4/1991 |
| DE | 4242889 A1 | 6/1994 |
| DE | 4409392 A1 | 9/1995 |
| DE | 4423257 | 1/1996 |
| DE | 19504867 C1 | 2/1996 |
| DE | 29913200 U1 | 9/1999 |
| DE | 202004020209 | 5/2006 |
| EP | 0179695 | 4/1986 |
| EP | 0425542 B1 | 5/1991 |
| EP | 0505634 A1 | 9/1992 |
| EP | 0517030 A2 | 12/1992 |

(56) References Cited

FOREIGN PATENT DOCUMENTS

| | | |
|---|---|---|
| EP | 0517030 A3 | 4/1993 |
| EP | 0577178 A1 | 1/1994 |
| EP | 0639351 A2 | 2/1995 |
| EP | 0639351 A3 | 3/1995 |
| EP | 0641547 B1 | 3/1995 |
| EP | 504346 B1 | 5/1995 |
| EP | 0517030 B1 | 9/1996 |
| EP | 0505634 B1 | 8/1997 |
| EP | 897697 A1 | 2/1999 |
| EP | 0966930 | 12/1999 |
| EP | 0968692 A1 | 1/2000 |
| EP | 0974319 | 1/2000 |
| EP | 0974319 A2 | 1/2000 |
| EP | 1033941 | 9/2000 |
| EP | 1051133 | 11/2000 |
| EP | 1103236 | 5/2001 |
| EP | 1402836 | 3/2004 |
| EP | 0906065 B1 | 9/2004 |
| EP | 1124512 | 9/2004 |
| EP | 1459711 | 7/2007 |
| EP | 1194087 | 8/2008 |
| FR | 2552659 | 4/1985 |
| FR | 2697996 | 5/1994 |
| FR | 2700947 | 8/1994 |
| FR | 2703580 A1 | 10/1994 |
| FR | 2727003 | 5/1996 |
| FR | 2747034 A1 | 10/1997 |
| FR | 2753368 | 3/1998 |
| GB | 157668 A | 1/1921 |
| GB | 265592 A | 8/1927 |
| GB | 2148122 A | 5/1985 |
| GB | 2207607 | 2/1989 |
| GB | 2239482 A | 7/1991 |
| GB | 2266246 A | 10/1993 |
| JP | 03-505416 | 11/1991 |
| JP | 9-280219 | 10/1997 |
| JP | 2006-513752 | 4/2006 |
| RU | 2229271 | 5/2004 |
| RU | 2244527 | 1/2005 |
| RU | 2307625 | 10/2007 |
| SU | 1465040 A1 | 3/1989 |
| WO | WO 88/03417 | 5/1988 |
| WO | WO 89/09035 | 10/1989 |
| WO | WO 90/00037 | 1/1990 |
| WO | WO 92/01428 | 2/1992 |
| WO | WO 92/06005 | 4/1992 |
| WO | WO 93/01771 | 2/1993 |
| WO | WO 95/26164 | 5/1994 |
| WO | WO 95/08964 | 4/1995 |
| WO | WO 95/15133 | 6/1995 |
| WO | WO 95/20370 | 8/1995 |
| WO | WO 95/21053 | 8/1995 |
| WO | WO 96/39988 | 12/1996 |
| WO | WO 96/40015 | 12/1996 |
| WO | WO 97/20526 | 6/1997 |
| WO | WO 97/23175 A | 7/1997 |
| WO | WO 97/25941 | 7/1997 |
| WO | WO 97/25945 | 7/1997 |
| WO | WO 97/37620 | 10/1997 |
| WO | WO 97/39693 | 10/1997 |
| WO | WO 98/17208 | 4/1998 |
| WO | WO 98/17209 | 4/1998 |
| WO | WO 88/10100 | 12/1998 |
| WO | WO 98/55052 | 12/1998 |
| WO | WO 98/56319 | 12/1998 |
| WO | WO 98/56433 | 12/1998 |
| WO | WO 99/09896 | 3/1999 |
| WO | WO 99/09903 | 3/1999 |
| WO | WO 99/27864 | 6/1999 |
| WO | WO 99/29271 | 6/1999 |
| WO | WO 99/63914 | 6/1999 |
| WO | WO 99/32055 | 7/1999 |
| WO | WO 99/38461 | 8/1999 |
| WO | WO 99/38463 A2 | 8/1999 |
| WO | WO 99/56675 | 11/1999 |
| WO | WO 00/07527 | 2/2000 |
| WO | WO 00/07528 | 2/2000 |
| WO | WO 00/25706 | 5/2000 |
| WO | WO 00/30568 | 6/2000 |
| WO | WO 00/40177 | 7/2000 |
| WO | WO 00/41654 | 7/2000 |
| WO | WO 00/59412 | 10/2000 |
| WO | WO 00/66044 A1 | 11/2000 |
| WO | WO 00/66045 A1 | 11/2000 |
| WO | WO 00/74607 A1 | 12/2000 |
| WO | WO 01/08611 | 2/2001 |
| WO | WO 01/56497 A2 | 8/2001 |
| WO | WO 01/62190 | 8/2001 |
| WO | WO 01/80785 | 11/2001 |
| WO | WO 01/56497 A3 | 12/2001 |
| WO | WO 01/93742 A2 | 12/2001 |
| WO | WO 01/95837 A1 | 12/2001 |
| WO | WO 01/56497 B1 | 3/2002 |
| WO | WO 01/93742 A3 | 9/2002 |
| WO | WO 2004/069106 | 8/2004 |
| WO | WO 2005/007040 A | 1/2005 |
| WO | WO 2005/020861 | 3/2005 |
| WO | WO 2006/138500 | 12/2006 |
| WO | WO 2007/098288 | 8/2007 |
| WO | WO 2008/014258 | 1/2008 |
| WO | WO 2008/082473 | 7/2008 |
| WO | WO 2008/124355 | 10/2008 |
| WO | WO 2008/154326 | 12/2008 |
| WO | WO 2009/064644 | 5/2009 |
| WO | WO 2010/054181 | 5/2010 |
| WO | WO 2010/054208 | 5/2010 |
| WO | WO 2012/088238 | 6/2012 |

OTHER PUBLICATIONS

U.S. Appl. No. 60/071,527, filed Jan. 15, 1998, Urbahns.
Synthes History and Evolution of LBIF Brochure; Nov. 2015, 30 pages.
Synthes Spine Cervical Stand-Alone Devices Presentation Brochure; 2010, 40 pages.
DePuy Motech Surgical Titanium Mesh Brochure; 1998, 13 pages.
AcroMed Carbon Fiber Interbody Fusion Devices; Jan. 1998, 8 pages.
Carbon Fiber Composite Ramps for Lumbar Interbody Fusion; Apr. 1997, 2 pages.
Al-Sanabani, Application of Calcium Phosphate Materials in Dentistry, vol. 2013, Int. J. Biomaterials, 1-12, 2013.
Bailey, Stabilzation of the Cervical Spine by Anterior Fusion, 42-A(4), J. Bone Joint Surg., 565-594, Jun. 1960.
Banward, Iliac Crest Bone Graft Harvest Donor Site Morbidity, 20 (9) Spine 1055-1060, May 1995.
Benezech, L'arthrodese Cervicale Par Voie Anterieure a L'Aide de Plaque-Cage P.C.B., 9(1) Rachis 1, 47, 1997 (w/Translation).
Brantigan I/F Cage for PLIF Surgical Technique Guide; Apr. 1991, 22 pages.
Brantigan, A Carbon Fiber Implant to Aid Interbody Lumbar Fusion, 16(6S) Spine S277- S282, Jul. 1991.
Brantigan, Compression Strength of Donor Bone for Posterior Lumbar Interbody Fusion, 18(9) Spine 1213-1221, 1993.
Brantigan, Interbody Lumbar Fusion Using a Carbon Fiber Cage Implant Versus Allograft Bone, 19(13) Spine 1436-1444, 1994.
Brantigan, Intervertebral Fusion, Chapter 27, Posterior Lumbar Interbody Fusion Using the Lumbar Interbody Fusion Cage, 437-466, 2006.
Brantigan, Pseudarthrosis Rate After Allograft Posterior Lumbar Interbody Fusion with Pedicle Screw and Plate Fixation, 19(11) Spine 1271-1280, Jun. 1994.
Cloward, Gas-Sterilized Cadaver Bone Grafts for Spinal Fusion Operations, 5(1) Spine 4-10 Jan./Feb. 1980.
Cloward, The Anterior Approach for Removal of Ruptured Cervical Disks, vol. 15, J. Neuro. 602-617, 1958.
Delecrin, Morbidite du Prelevement de Greffons osseuz au Niveau des Cretes Iliaques dans la Chirurgie Du Rachis; Justification du recours aux substituts osseux, 13(3) Rachis 167-174, 2001 (w/Translation).

(56) References Cited

OTHER PUBLICATIONS

Dereymaeker, Nouvelle Cure neuro-Chirurgicale de discopathies Cervicales, 2 Neurochirurgie 226-234; 1956 (w/Translation).
Dickman, Internal Fixation and Fusion of the Lumbar Spine Using Threaded Interbody Cages, 13(3) Barrow Quarterly (1997); http://www.thebarrow.org/Education_And_Resources/Barrow_Quarterly/204837.
Enker, Interbody Fusion and Instrumentation, No. 300 Clin. Orth. Rel. Res. 90-101, Mar. 1994.
Fassio, Use of Cervical Plate-Cage PCB and Results for Anterior Fusion in Cervical Disk Syndrome, 15(6) Rachis 355-361, Dec. 2003 Translation.
Fowler, Complications Associated with Harvesting Autogenous Iliac Bone Graft, 24(12) Am. J. Ortho. 895-904, Dec. 1995.
Fuentes, Les Complications de la Chirurgie Par Voie Anterieure du Rachis Cervical, 8(1) Rachis 3-14, 1996 (w/Translation).
Germay, Resultats Cliniques de Ceramiques D'hydroxyapatite dans les arthrodeses Inter-somatiques du Rachis Cervical Par Voie Anterieure. Etude Retrospective a Propose de 67 cas. 13(3), Rachis 189-195, 2001 (w/Translation).
Graham, Lateral Extracavitary Approach to the Thoracic and Thoracolumbar Spine, 20(7) Orthopedics, 605-610, Jul. 1997.
Gunatillake, Biodegradable Synthetic Polymers for Tissue Engineering, vol. 5, Eur. Cells Materials, 1-16, 2003.
Huttner, Spinal Stenosis & Posterior Lumbar Interbody Fusion, No. 193, Clinical Ortho Rel. Res. 103-114, Mar. 1985.
Jost, Compressive Strength of Interbody Cages in the Lumbar Spine: the Effect of Cage Shape, Posterior Instrumentation and Bone Density, 7 Eur. Spine J. 132-141, 1998.
Kastner, Advanced X-Ray Tomographic Methods for Quantitative Charecterisation of Carbon Fibre Reinforced Polymers, 4th Annual Intern. Symposium on NDT in Aerospace, 2012, 9 pages.
Khan, Chapter 2—Implantable Medical Devices, Focal Controlled Drug Delivery, Advances in Delivery Science and Technology, A.J. Domb and W. Khan (eds.) 2014.
Kozak, Anterior Lumbar Fusion Options, No, 300, Clin. Orth. Rel. Res., 45-51, 1994.
Kroppenstedt, Radiological Comparison of Instrumented Posterior Lumbar Interbody Fusion with One or Two Closed-Box Plasmapore Coated Titanium Cages, 33(19) Spine, 2083-2088, Sep. 2008.
Lund, Interbody Cage Stabilisation in the Lumbar Spine, 80-B(2) J Bone Joint Surg., 351-359, Mar. 1998.
Lyu, Degradability of Polymers for Implantable Biomedical Devices, 10, Int. J. Mol. Sci., 4033-4065, 2009.
Malca, Cervical Interbody Xenograft with Plate Fixation, 21(6) Spine, 685-690, Mar. 1996.
McAfee, Minimally Invasive Anterior Retroperitoneal Approach to the Lumbar Spine, 21(13) Spine, 1476-1484, 1998.
Nasca, Newer Lumbar Interbody Fusion Techniques, 22(2) J. Surg. Ortho. Advances, 113-117, 2013.
PCB Evolution Surgical Technique Guide 2010.
Polysciences Inc. Info Sheet 2012.
Porex Website, http://www.porex.com/technologies/materials/porous-plastics, Porous Plastic Materials, accessed Aug. 21, 2015, 2 pages.
Samandouras, A New Anterior Cervical Instrumentation System Combining an Intradiscal Cage with an Integrated Plate, 26(10) Spine, 1188-1192, 2001.
Sonntag, Controversy in Spine Care, Is Fusion Necessary After Anterior Cervical Discectomy 21(9) Spine, 1111-1113, May 1996.
Tamariz, Biodegradation of Medical Purpose Polymeric Materials and Their Impact on Biocompatibility, Chapter 1, Intech-bio degradation Life of Science, 2013; 28 pages.
Tan, A Modified Technique of Anterior Lumbar Fusion with Femoral Cortical Allograft, 5(3) J. Ortho. Surg. Tech., 83-93, 1990.
Verbiest H., La Chirurgie Anterieure et Laterale du Rachis Cervical,16(S2) Neurochirurgie 1-212; 1970 (w/Translation).
Wang, Increased Fusion Rates with Cervical Plating for Two-Level Anterior Cervical Discectomy and Fusion, 25(1) Spine 41-45, Jan. 2000.
Watters, Anterior Cervical Discectomy with and without Fusion, 19(20) Spine 2343-2347 Oct. 1994.
Weiner, Spinde Update Lumbar Interbody Cages, 23(5) Spine, 634-640, Mar. 1998.
White, Relief of Pain by Anterior Cervical-Spine Fusion for Spondylosis, 55-A(3) J. Bone Joint Surg. 525-534, Apr. 1973.
Whitesides, Lateral Approach to the Upper Cervical Spine for Anterior Fusion, vol. 59, South Med J, 879-883, Aug. 1966.
Wilson, Anterior Cervical Discectomy without Bone Graft, 47(4) J. Neurosurg. 551-555, Oct. 1977.
Younger, Morbidity at Bone Graft Donor Sites, 3(3) J. Orth. Trauma, 192-195, 1989.
Dabrowski, Highly Porous Titanium Scaffolds for Orthopaedic Applications, J. Biomed Mater. Res. B. Appl. Biomat. Oct;95(1):53-61, 2010.
Takahama, A New Improved Biodegradable Tracheal Prosthesis Using Hydroxy Apatite and Carbon Fiber 35(3) ASAIO Trans, 291-293, Jul.-Sep. 1989.
Wang, Determination of Cortical Bone Porosity and Pore Size Distribution using a Low Field Pulsed NMR Approach, J. Orthop Res., Mar; 21(2):312-9 Mar. 2003.
U.S. Appl. No. 11/199,599: Amendment/Request for Reconsideration after Non-Final Rejection, dated Sep. 29, 2009, 30 pages.
U.S. Appl. No. 11/199,599: Appeal Brief, dated Apr. 15, 2010, 51 pages.
U.S. Appl. No. 11/199,599: Final Rejection, dated Dec. 24, 2009, 21 pages.
U.S. Appl. No. 11/199,599: Interview Summary included Draft Amendments, dated Sep. 24, 2009, 16 pages.
U.S. Appl. No. 11/199,599: Non-Final Rejection, dated Apr. 1, 2009, 20 pages.
U.S. Appl. No. 11/199,599: Preliminary Amendment, dated Jan. 9, 2008, 11 pages.
"Jury Trial Demanded", In the United States District Court for the District of Delaware, Case No. 1:11-cv-00652-LPS, filed Jul. 22, 2011, 8 pages.
Chadwick et al., "Radiolucent Structural Materials for Medical Applications," www.mddionline.com/print/238, Jun. 1, 2001, accsessed date Jul. 31, 2012, 9 pages.
Jonbergen et al., "Anterior Cervical Interbody fusion with a titanium box cage: Early radiological assessment of fusion and subsidence", The Spine Journal 5, Jul. 2005, 645-649.
Marcolongo et al., "Trends in Materials for Spine Surgery", Biomaterials and Clinical Use, 6, 2011, 21 pages.
Parlov et al., "Anterior Lumbar Interbody Fusion with Threaded Fusion Cages and Autologous Grafts", Eur. Spine J., Jun. 2000, 9, 224-229.
Schleicher et al., "Biomechanical Comparison of Two Different Concepts for Stand alone anterior lumbar interbody fusion", Eur. Spine J., Sep. 2008, 17, 1757-1765.
Scholz et al., "A New Stand-Alone Cervical Anterior Interbody Fusion Device", Spine, Jan. 2009, 34(2), 6 pages.
Spruit et al., "The in Vitro Stabilising Effect of Polyetheretherketone Cages Versus a Titanium Cage of similar design for anterior lumbar interbody fusion", Eur. Spine J., Aug. 2005, 14 752-758.
"Expert Report of Paul Ducheyne, PH.D. Concerning Patent Validity", United States District Court District of Delaware, Civil Action No. 1:11-cv-00652-LPS, Dec. 13, 2012, 155 pages.
"Expert Report of Richard J. Gering, Ph.D., CLP", In the United States District Court for the District of Delaware, Civil Action No. 1:11-cv-00652-LPS, Dec. 14, 2012, 39 pages.
"Expert Report of John F. Hall, M.D.", United States District Court for the District of Delaware, Civil Action No. 1:11-cv-00652-LPS, Dec. 14, 2012, 27 pages.
"Second Expert Report of Wilson C. Hayes, Ph.D.", United States District Court for the District of Delaware, Civil Action No. 1:11-cv-00652-LPS, Dec. 14, 2012, 22 pages.
"Expert Report of Dr. Domagoj Coric Regarding the Invalidity of U.S. Pat. No. 7,846,207, U.S. Pat. No. 7,862,616 and U.S. Pat. No. 7,875,076", in the United States District Court for the District of Delaware, Civil Action No. 1:11-cv-00652-LPS, Nov. 5, 2012, 149 pages.

(56) References Cited

OTHER PUBLICATIONS

"Reply Report of Dr. Domagoj Coric Regarding the Invalidity of U.S. Pat. No. 7,846,207, U.S. Pat. No. 7,862,616 and U.S. Pat. No. 7,875,076", in the United States District Court for the District of Delaware, Civil Action No. 1:11-cv-00652-LPS, Jan. 4, 2013, 81 pages.
"Joint Claim Construction Brief", In the United States District Court for the District of Delaware, Civil Action No. 1:11-cv-00652-LPS, Jun. 14, 2012, 97 pages.
"Plaintiffs' Responses and Objections to Defendant Globus Medical, Inc.'s First Set of Interrogatories (Nos. 1-11)", United States District Court for the District of Delaware, Civil Action No. 1:11-cv-00652-LPS, Nov. 14, 2011, 18 pages.
"Plaintiffs' Supplemental Responses and Objections to Defendant Globus Medical Inc.'s Interrogatories Nos. 6-10 and Second Supplemental Responses and Objections to Interrogatory No. 5", United States District Court for the District of Delaware, Civil Action No. 11-cv-652-LPS, Sep. 1, 2012, 12 pages.
"Appendix 1 to Joint Claim Construction Brief; Synthes' Exhibits A-9", In the United States District Court for the District of Delaware Civil Action No. 1:11-cv-00652-LPS, Jun. 8, 2012, 192 pages.
"Appendix 2 to Joint Claim Construction Brief; Globus' Exhibits A-F", In the United States District Court for the District of Delaware Civil Action No. 1:11-cv-00652-LPS, Jun. 8, 2012, 146 pages.
"Appendix 3 to Joint Claim Construction Brief; Exhibits A-C", In the United States District Court for the District of Delaware Civil Action No. 1:11-cv-00652-LPS, Jun. 8, 2012, 38 pages.
Trial Transcript, United States District Court District of Delaware, Civil Action No. 1:11-cv00652-LPS, Jun. 3, 2013, 98 pages.
Trial Transcript, United States District Court District of Delaware, Civil Action No. 1:11-cv-00652-LPS, Jun. 4, 2013, 110 pages.
Trial Transcript, United States District Court District of Delaware, Civil Action No. 1:11-cv-00652-LPS, Jun. 5, 2013, 99 pages.
Trial Transcript, United States District Court District of Delaware, Civil Action No. 1:11-cv-00652-LPS, Jun. 6, 2013, 80 pages.
Trial Transcript, United States District Court District of Delaware, Civil Action No. 1:11-cv-00652-LPS, Jun. 7, 2013, 97 pages.
Trial Transcript, United States District Court District of Delaware, Civil Action No. 1:11-cv-00652-LPS, Jun. 10, 2013, 114 pages.
Trial Transcript, United States District Court District of Delaware, Civil Action No. 1:11-cv-00652-LPS, Jun. 11, 2013, 98 pages.
Trial Transcript, United States District Court District of Delaware, Civil Action No. 1:11-cv-00652-LPS, Jun. 12, 2013, 75 pages.
Trial Transcript, United States District Court District of Delaware, Civil Action No. 1:11-cv-00652-LPS, Jun. 13, 2013, 94 pages.
Trial Transcript, United States District Court District of Delaware, Civil Action No. 1:11-cv-00652-LPS, Jun. 14, 2013, 26 pages.
Jury Verdict Form, United States District Court District of Delaware, Civil Action No. 1:11-cv-00652-LPS, Jun. 14, 2013, 20 pages.
"Memorandum Opinion" United States District Court District of Delaware, Civil Action No. 1:11-cv-00652-LPS, May 7, 2013, 33 pages.
"Order" United States District Court District of Delaware, Civil Action No. 1:11-cv-00652-LPS, May 7, 2013, 7 pages.
Redacted version of "Opening Brief in Support of Plaintiffs' Motion for Summary Judgment of No Anticipation by the Kozak and Michelson References", United States District Court District of Delaware, Civil Action No. 1:11-cv-00652-LPS, Feb. 13, 2013, 66 pages.
Redacted version of "Defendant Globus Medical, Inc.'s Answering Brief in Opposition to Plaintiff's Motion for Summary Judgment of No Anticipation by the Kozak and Michelson References", Mar. 12, 2013, 233 pages.
Redacted version of "Plaintiff's Reply Brief in Support of Plaintiff's Motion for Summary Judgment of No Anticipation by the Kozak and Michelson References", Mar. 21, 2013, 11 pages.
"Order" United States District Court District of Delaware, Civil Action No. 1:11-cv-00652-LPS, May 15, 2013, 4 pages.
International Patent Application No. PCT/CH2003/00089, International Search Report dated Dec. 2, 2003, 3 pgs.
International Search Report, completed Aug. 16, 2007 for International Application No. PCT/US2007/005098, filed Feb. 27, 2007.
U.S. Appl. No. 60/988,661, filed Nov. 16, 2007, Kueenzi et al.
U.S. Appl. No. 61/535,726, filed Sep. 16, 2011, Zaveloff.
Japanese Patent Application No. 2011-534926: Office Action dated Oct. 30, 2013, 7 pages.
Japanese Patent Application No. 2011-534928: Office Action dated Sep. 30, 2013, 11 pages.
Russian Patent Application No. 2011-1122797: Decision to Grant dated Oct. 9, 2013, 20 pages.
Synthes Spine, "SynFix-LR System. Instruments and Implants for Stand-Alone Anterior Lumbar Interbody Fusion (ALIF)", Technique Guide dated 2008, pp. 2-40, Published by Synthes Spine (USA).
Synthes Spine, "Zero-P Instruments and Implants. Zero-Profile Anterior Cervical Interbody Fusion (ACIF) device", Technique Guide dated 2008, pp. 2-32, Published by Synthes Spine (USA).
Bray, "InterPlate Spine Fusion Device: Subsidence Control Without Stress Shielding", Orthopaedic Product News, Sep./Oct. 2006, pp. 22-25.
International Search Report, Mailed Mar. 20, 2009, for PCT International Application No. PCT/US80/82473, filed Nov. 5, 2008.
Written Opinion, Mailed Mar. 20, 2009, for PCT International Application No. PCT/US08/82473, filed Nov. 5, 2008.
Synthes Spine, "CorticoCancellous ACF Spacer. An allograft space or anterior fusion of the cervical spine," brochure, Musculoskeletal Transplant Foundationm, 2003, 6 pages.
International Patent Application PCT/US2011/066421, International Search Report dated Jun. 14, 2012, 31 pages.

* cited by examiner

INTERVERTEBRAL IMPLANT

CROSS REFERENCE TO RELATED APPLICATIONS

This application is a continuation of U.S. application Ser. No. 12/969,330 filed Dec. 15, 2010, which is a continuation of U.S. application Ser. No. 12/432,088 filed Apr. 29, 2009, now U.S. Pat. No. 7,862,616 issued Jan. 4, 2011, which is a continuation of U.S. application Ser. No. 11/199,599 filed Aug. 8, 2005, now U.S. Pat. No. 7,846,207 issued Dec. 7, 2010, which is a continuation of International Application No. PCT/CH2003/000089 filed Feb. 6, 2003, the disclosures of which are incorporated herein by reference in their entireties.

TECHNICAL FIELD

The present invention relates generally to intervertebral implants.

BACKGROUND OF THE INVENTION

GB-A-2 207 607 discloses an intervertebral implant, which has a horseshoe-shaped configuration with a plurality of cylindrical holes. The holes are smooth on the inside and only have a stop for the heads of the bone screws, which are to be introduced therein. A disadvantage of this arrangement is that the fastening screws, introduced therein, can be anchored only with their shaft in the bone. This does not result in a rigid connection with the horseshoe-shaped intervertebral implant. When the anchoring of the screw shaft in the bone is weakened, the intervertebral implant becomes movable with respect to the screw and the bone screws tend to migrate, endangering the blood vessels. Moreover, the loosening of the intervertebral implant can lead to a pseudoarthrosis.

U.S. Patent Publication US-A 2000/0010511 (Michelson) discloses an intervertebral implant, which, at its front surface, has two boreholes with an internal thread, into which bone screws with a threaded head can be introduced. A disadvantage of this implant is that the bone screws can become loose and are not secured against being screwed out or falling out. A further disadvantage is that the bone screws are fastened completely to the implant body itself and that therefore the latter experiences a relatively large stress.

Screws which emerge at the anterior or anterolateral edge of the vertebral body because of loosening run the risk of injuring main vessels such as the aorta and Vena calva, as well as supply vessels such as lumbar arteries and veins. Injury to these main vessels may result in internal bleeding possibly causing death within a very short time. Loosening of screws is more likely when they are not mounted angularly firmly.

SUMMARY OF THE INVENTION

The present invention is to provide a remedy for the above-discussed disadvantages. The present invention is directed to an intervertebral implant which can enter into a permanent, rigid connection with bone fixation means, so that, even if the bone structure is weakened, there is no loosening between the intervertebral implant and the bone fixation means. Moreover, over a separately constructed front plate, there is tension chording for the bone fixation elements, so that the implant body experiences less stress, that is, superimposed tensions. Moreover, a securing plate enables all bone fixation elements to be secured simultaneously.

The present invention accomplishes the objective set out above with an intervertebral implant, comprising a three-dimensional body having an upper side and an under side which are suitable for abutting the end plates of two adjacent vertebral bodies. The three-dimensional body further includes a left side surface and a right side surface, a front surface and a rear surface, a horizontal middle plane between the upper side and the under side, and a vertical middle plane extending from the front surface to the rear surface. The three-dimensional body further comprising a plurality of boreholes, having openings at least at or near the front surface, passing there through and being suitable for accommodating longitudinal fixation elements. The intervertebral implant further including a front plate displaceably disposed as an insert with the front side of the three-dimensional body, where the front plate includes a plurality of boreholes having openings and in which the longitudinal fixation elements can be anchored, and whose openings overlap with the openings of the boreholes of the three-dimensional body. The intervertebral implant has a securing plate fastened substantially parallel to the front plate in such a manner that the boreholes of the front plate are covered at least partly by the securing plate. An advantage achieved by the present invention, arises essentially from the solid connection between the intervertebral implant and the longitudinal fixation elements, used to fasten it.

Compared to the two-part implants of the state of the art, for which a front plate is implanted in a separate step, the present invention has the advantage that the implantation of the intervertebral implant may be carried out in one step and, with that, can be carried out more easily and more quickly. A further advantage is that the intervertebral implant is fixed as frontally as possible at the body of the vertebra. That is, at a place where good bone material usually is present. The result is an anterior movement limitation without a greater risk to the surrounding structures. The load is still absorbed under compression by the intervertebral implant and not by the front plate or the fixation screws (longitudinal fixation elements).

A method for implanting an intervertebral implant of the present invention between two adjacent vertebral bodies includes introducing the intervertebral implant, having a three-dimensional body, a front plate, and one or more boreholes, between two adjacent vertebral bodies, attaching longitudinal fixation elements with heads through the boreholes into the vertebral bodies, and attaching a securing plate by means of a fastening agent over the heads of the longitudinal fixation elements to the front plate, such that the heads of the longitudinal fixation elements are captured between the front plate and the securing plate wherein the longitudinal fixation elements are secured against being shifted relative to the intervertebral implant.

Other objectives and advantages in addition to those discussed above will become apparent to those skilled in the art during the course of the description of a preferred embodiment of the invention which follows. In the description, reference is made to accompanying drawings, which form a part thereof, and which illustrate an example of the invention. Such example, however, is not exhaustive of the various embodiments of the invention, and therefore, reference is made to the claims that follow the description for determining the scope of the invention.

DESCRIPTION OF PREFERRED EMBODIMENTS

Figure 1:
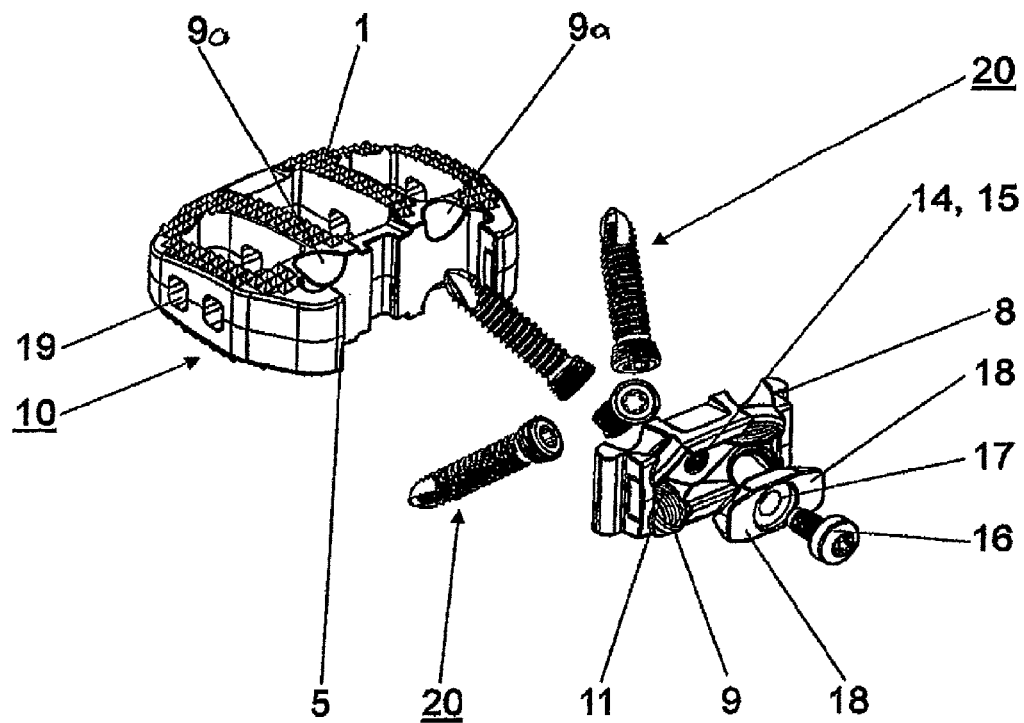
FIG. 1 shows an exploded drawing of the intervertebral implant.

The intervertebral implant, shown in FIG. 1-7, includes a three-dimensional body 10 in the form of a cage with an upper side 1 and an underside 2, which are suitable for abutting the end plates of two adjacent vertebral bodies, a left side surface 3 and a right side surface 4, a front surface 5 and a back surface 6, a horizontal middle plane 7 located between the upper side 1 and the underside 2, a vertical middle plane 12 extending from the front surface 5 to the rear surface 6 and four boreholes 9a, which pass through the body 10 and are suitable for accommodating longitudinal fixation elements 20. The body 10 may be constructed as a hollow body, the mantle surfaces of which are provided with perforations 19. The upper side 1 and/or under side 2 of the intervertebral implant may preferably be convex in shape, not planar. A convex shape to the upper side 1 and the underside 2 allows for an improved fit with the end plates of the adjacent vertebral bodies by the intervertebral implant. Further, the side surfaces 1-6 of the intervertebral implant may be essentially convex, as well.

Figure 7:
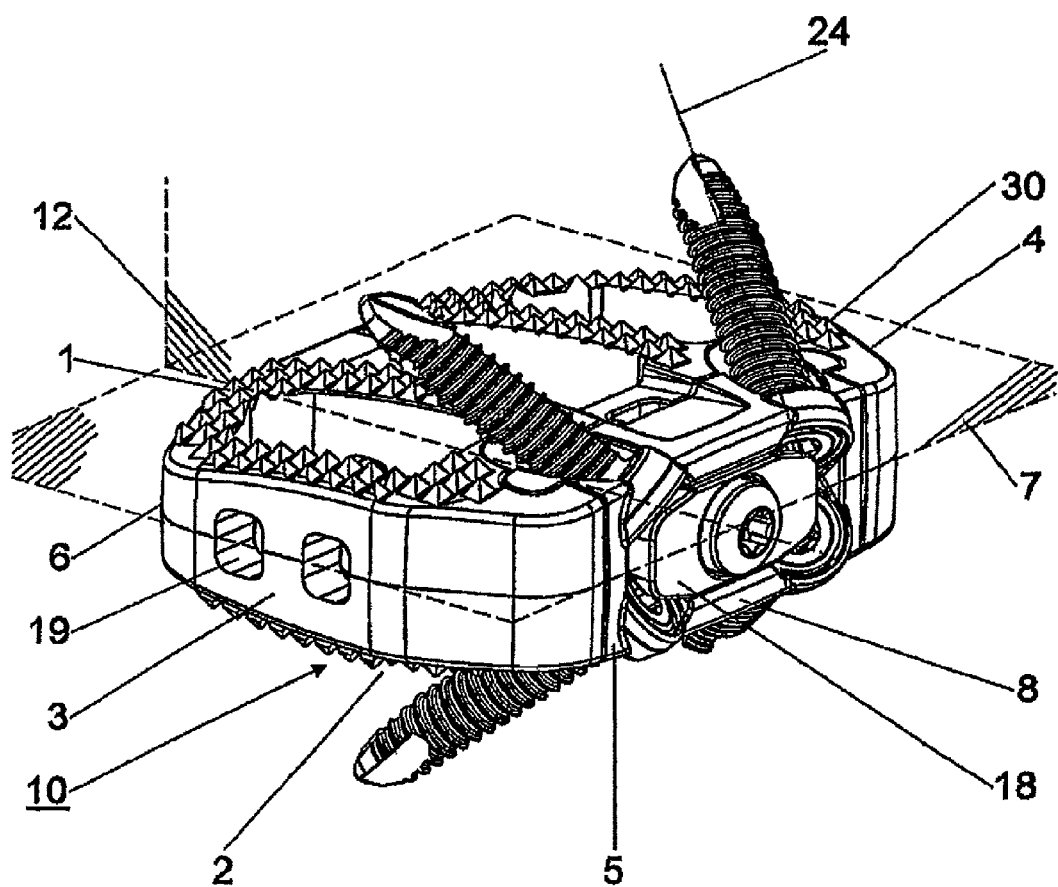
FIG. 7 shows a completely installed intervertebral implant with front plate and securing plate.

As shown in FIG. 7, the upper side 1 and the underside 2 of the three-dimensional body 10 are provided with structuring in the form of teeth 30.

Figure 5:
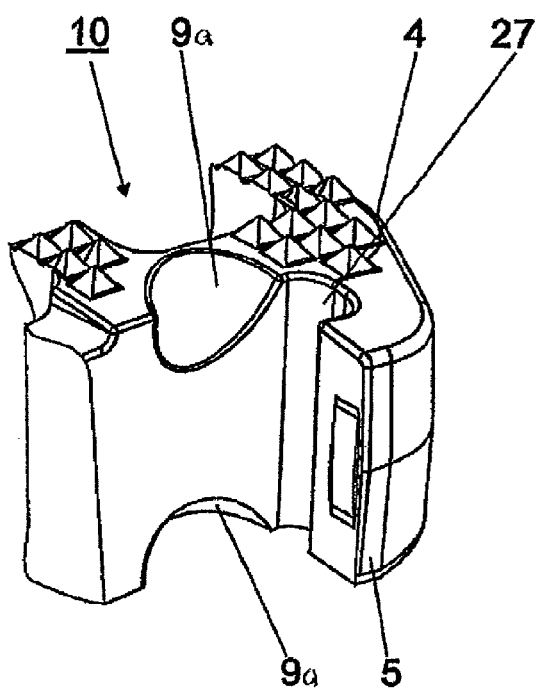
FIG. 5 shows a three-dimensional detailed representation of the body of the intervertebral implant, which shows the connecting elements to the front plate of FIG. 6.
Figure 6:
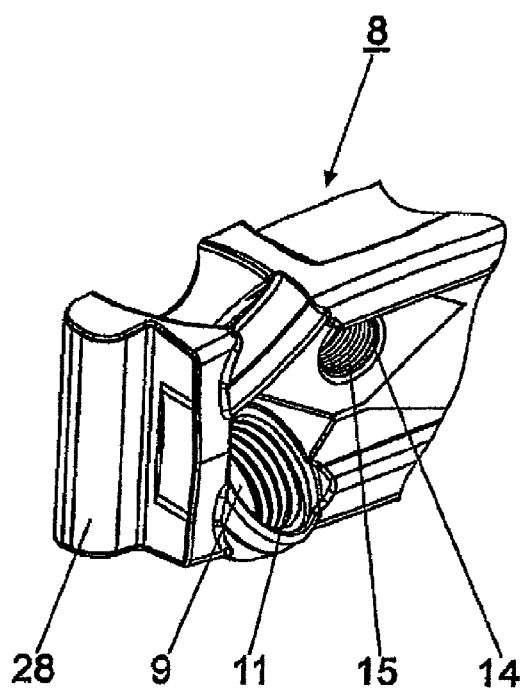
FIG. 6 shows a three-dimensional detailed representation of the front plate of the intervertebral implant and the connecting elements to the body of FIG. 5

At the front surface of the three-dimensional body 10, a front plate 8 may be mounted, which is disposed perpendicular to the horizontal central plane of the intervertebral implant and through which four boreholes 9 pass and in which the longitudinal fixation elements 20 can be anchored. The front plate 8, as shown in FIGS. 5 and 6, is constructed as an insert for the three-dimensional body 10. The three-dimensional body 10 has a semicircular groove 27 extending parallel to the vertical middle plane 12 at the transitions of the left side surface 3 and the right side surface 4 (FIG. 5) to the front surface 5. Correspondingly, the front plate 8 has right and left (FIG. 6) similarly extending and similarly dimensioned, semicircular rail 28. As a result, the front plate can be pushed and positioned easily with its two lateral rails 28 into the corresponding grooves 27 of the body 10 during the production of the intervertebral implant.

In one embodiment, at least one of the boreholes 9 in the front plate is constructed so that a longitudinal fixation element 20, accommodated therein, can be connected rigidly with the front plate. A rigid connection may be accomplished, for example, owing to the fact that at least one of the boreholes 9 of the front plate 8 has an internal thread. A corresponding longitudinal fixation element 20, bone screw, with a threaded end can then be screwed together rigidly with the implant. In an alternative embodiment, the four boreholes 9 in the front plate may have an internal thread 11, so that longitudinal fixation elements 20 can be connected rigidly with the front plate 8.

As discussed, the front plate 8 may be disposed, preferably vertically to the horizontal central plane, so that it can be displaced vertically with respect to the three-dimensional body 10. By these means, "stress shielding" (protection and neutralization of mechanical stresses) is attained, which permits the end plates to be adapted to the intervertebral implant during the healing process.

The intervertebral implant may have a securing plate 18, which can be fastened by means of a screw connection parallel to the front plate 8 at the front plate 8 in such a manner that the boreholes 9 of the front plate 8 are partly covered by the securing plate 18. The securing plate 18 may have a central borehole 17 provided, preferably, with an internal thread. Corresponding thereto, the front plate 8 has a central borehole 15 for accommodating fastening means 16. Preferably, the central borehole 15 has an internal thread 14 for accommodating a fastening means 16 in the form of a screw. The securing plate 18 may also be fastened by a bayonet catch or a click catch. By fastening the securing plate 18 to the front plate 8, the heads 21 of the longitudinal fixation elements 20 (discussed later) are contacted by the securing plate 18, so that they are secured against being ejected or screwed out.

Figure 3:
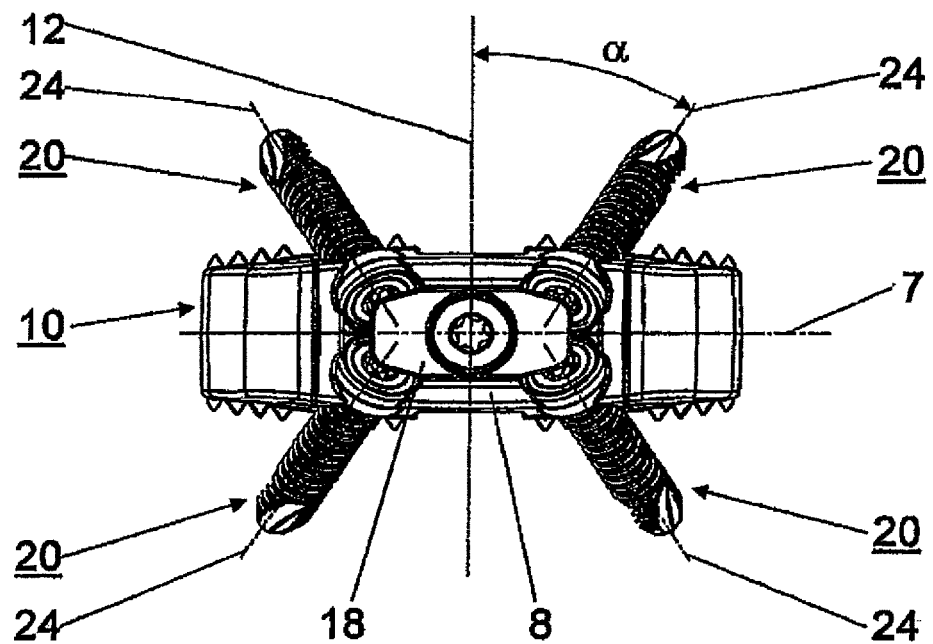
FIG. 3 shows an elevation of the intervertebral implant of FIG. 1.
Figure 4:
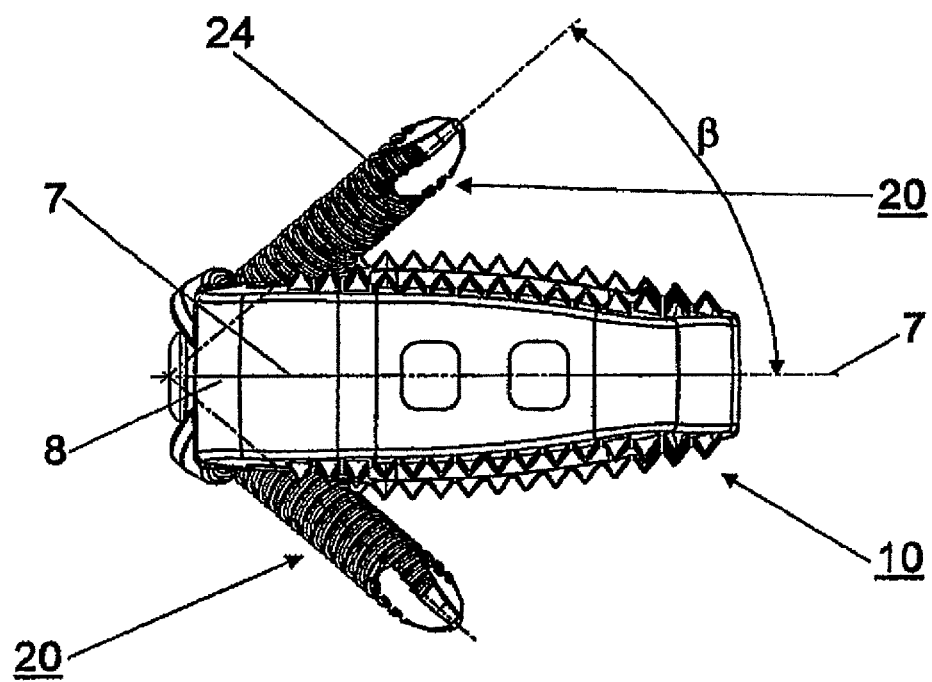
FIG. 4 shows a side view of the intervertebral implant of FIG. 1.

Preferably, the boreholes 9a of the three-dimensional body 10 do not pass either through the left side surface 3 or the right side surface 4 or completely through the front surface 5. The front surface 5, preferably, is also not crossed by the boreholes 9a. Further, the horizontal middle plane 7 is not pierced by the boreholes 9a. Only the axes 24 of the longitudinal fixation elements 20, introduced therein, intersect the horizontal middle plane 7 of the body 10. As seen from the front surface 5, the boreholes of the three-dimensional body 10 and the front plate diverge. The axes 24 of the boreholes of the three-dimensional plate 10 and the front plate 8 enclose an angle β ranging from 20° to 60°, specifically from 36° to 48°, and more preferably an angle β of 42° with the horizontal middle plane 7 (FIG. 4) and an angle α ranging from 10° to 45°, specifically from 27° to 33°, and more preferably an angle α of 30° with the vertical middle plane 12 (FIG. 3). Thus, better access for introducing the screws is achieved.

In one embodiment, at least one of the boreholes 9 of the front plate 8 may taper conically towards the underside 2, so that a bone screw, with a corresponding conical head, can be anchored rigidly therein. The conical borehole preferably has a conical angle, which is smaller than the resulting frictional angle. Advisably, the conicity of the conical borehole is 1:3.75 to 1:20.00 and preferably 1:5 to 1:15.

In another configuration, at least two of the boreholes 9 of the front plate 8 extend parallel to each other. This makes insertion of the intervertebral implant easier. In another embodiment, at least two of the boreholes 9 of the front plate 8 diverge when viewed from the front side. By these means, a region of the vertebral body, which has a better bone quality than does the center of the vertebral body, is reached by the bone screws.

To improve the anchoring of the bone screw in a plastic body of the intervertebral implant (discussed later), a metal sleeve with an internal thread (not shown) may be inserted in the boreholes of the front plate and three-dimensional body. The intervertebral implant may also consist only partially of an x-ray transparent plastic and, in the region of the boreholes consist of a metal, such as titanium or a titanium alloy. Improved guidance and anchoring of the bone screws in the intervertebral implant may be achieved. Further, the boreholes 9 may have a smooth internal wall, into which the threaded head of a metallic, longitudinal fixation element may cut or be molded.

Depending on circumstances, two, three, four or more longitudinal fixation elements may be connected rigidly with the intervertebral implant. Preferably, at least one fixation element should pierce the upper side and at least one fixation element the underside of the intervertebral implant. The longitudinal fixation elements 20 may have either a smooth head, so that there will not be a rigid connection with the implant or a threaded, conical or expendable end, so that there will be a rigid connection with the implant. In both cases, however, the longitudinal fixation elements 20 are secured by the securing plate against rotating out, being ejected out or falling out at a later time.

Figure 2:
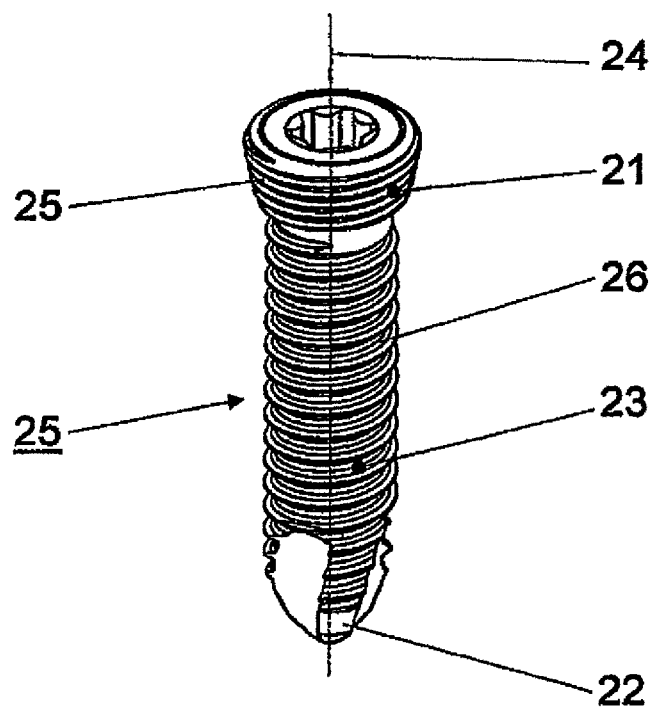
FIG. 2 shows a longitudinal fixation element in the form of a screw.

The longitudinal fixation elements 20 are preferably constructed as bone screws. As shown in FIG. 2, the longitudinal fixation elements 20, introduced into the boreholes 9, have a head 21, a tip 22, a shaft 23 and an axis 24. The head 21 may preferably be provided with an external thread 25, which corresponds to the internal thread 11 of the borehole 9, so that the heads 21 can be anchored in the boreholes 9 in a rigid manner. The shaft 23 may be provided with a thread 26, which is self-drilling and self-cutting. The load thread angle of the thread 26 has a range of between 11° to 14°, preferably between 12° and 13°, and more preferably a load thread angle of 115°. The pitch angle of the thread may have a range of between 6° and 10°, preferably between 7° and 9°, and more preferably have a pitch angle of 8°. The special pitch angle produces a self-retardation in the thread, thus ensuring that the bone screw will not automatically become loose.

In the case of a second, possibly rigid type of connection, a longitudinal fixation element 20, bone screw, may preferably be used, the head of which tapers conically towards the shaft, the conicity of the head corresponding to the conicity of the borehole of the intervertebral implant. The longitudinal fixation elements may also be constructed as threadless cylindrical pins, which are provided with a drilling tip, preferably in the form of a trocar. A further variation consist therein that the longitudinal fixation elements are constructed as spiral springs. Finally, the longitudinal fixation elements may also be constructed as single-vaned or multi-vaned spiral blades.

As shown in FIG. 7, two longitudinal fixation elements 20 pierce the upper side 1 and two longitudinal fixation elements 20 pierce the underside 2 of the body 10, thereby anchoring the intervertebral implant to the adjacent vertebral bodies.

The intervertebral implant may be produced from any material which is compatible with the body. Preferably, the three-dimensional body 10 may consist of a body-compatible plastic which has not been reinforced and which may be transparent to x-rays. The advantage over fiber-reinforced plastics, which are already known in implant technology, is that no reinforcing fibers are exposed. Such exposure may be disadvantageous clinically. In such a three-dimensional body 10 constructed of a plastic that has not been reinforced, the use bone screws may be preferable. As discussed previously, the external thread of the bone screw(s) may have a load thread angle range of 11° to 14°, and preferably between 12° to 13°. A comparatively slight inclination of the load flank brings about a high clamping force. As a result, radial expansion and the danger of forming cracks in the plastic are reduced. Furthermore, the external thread of the bone screw(s) may preferably have a pitch angle between 6° and 10° and preferably between 7° and 9°.

The front plate 8 may be made from materials different than the three-dimensional body 10. The front plate 8 is preferably made from a metallic material. Titanium or titanium alloys are particularly suitable as metallic materials. The complete tension chord arrangement (front plate and screws) may also be made from implant steel or highly alloyed metallic materials, such as CoCrMo or CoCrMoC. The advantage of titanium lies in that there is good tissue compatibility and the good ingrowing behavior of bones. The advantage of highly alloyed metallic materials lies in their high-strength values, which permit filigree constructions.

A brief description of a surgical procedure follows in order to explain the invention further.

The intervertebral implant, in the form of a three-dimensional body 10, is introduced between two adjacent vertebral bodies by means of a suitable instrument. Longitudinal fixation elements 20, in the form of bone screws, securing the three-dimensional body 10 are screwed/inserted by means of a suitable aiming device through the boreholes 9 of the front plate 8 into the vertebral bodies. The front plate 8 may be displaced vertically with respect to the three-dimensional body 10, such that the openings of the boreholes 9a of the three-dimensional plate 10 and the boreholes 9 of the front plate 8 overlap, to obtain stress shielding. The securing plate 18 is fastened by means of the fastening agent 16 in the form of a screw over the heads 21 of the longitudinal fixation elements 20 at the front plate 8, so that the heads 21 of the longitudinal fixation elements 20 and, with that, the screws themselves, are captured between the front plate 8 and the securing plate 18 and secured against being shifted relative to the three-dimensional body 10 (for example, by falling out or by turning out). The fastening agent 16, in the form of a screw, preferably is provided with a thread, which is distinguished by a large self-retardation.

What is claimed:

1. An intervertebral implant configured to be inserted into an intervertebral space that is defined by a first vertebral body and a second vertebral body, the intervertebral implant comprising:

(a) a body defining a rear body surface, a front body surface spaced from the rear body surface in a forward direction, an upper body surface, a lower body surface spaced from the upper body surface along a vertical direction that is perpendicular to the forward direction such that the upper body surface is spaced from the lower body surface a first maximum distance along the vertical direction, the body including a first recess defined by both the front body surface and the upper body surface, and a second recess defined by both the front body surface and the lower body surface, wherein the body is configured such that when the intervertebral implant is inserted into the intervertebral space: 1) at least a portion of the upper body surface contacts an endplate of the first vertebral body; and 2) at least a portion of the lower body surface contacts an endplate of the second vertebral body; and (b) a plate comprising a biocompatible material, the plate defining a rear plate surface and a front plate surface that is spaced from the rear plate surface, an upper plate surface and a lower plate surface spaced from the upper plate surface, wherein the plate defines:

i. a first plate hole configured to receive a portion of a first bone fixation element such that the first bone fixation element passes through the endplate of the first vertebral body, the first plate hole including a first opening in the front plate surface and a second opening in the upper plate surface; and ii. a second plate hole configured to receive a portion of a second bone fixation element such that the second bone fixation element passes through the endplate of the second vertebral body, the second plate hole including a third opening in the front plate surface and a fourth opening in the lower plate surface;

wherein the plate is configured to be mounted to the body such that the rear plate surface faces the body and at least a portion of the plate is recessed with respect to a portion of the front body surface in a rearward direction that is opposite the forward direction, and when the plate is mounted to the body:

i. at least a portion of the upper plate surface is configured to face the endplate of the first vertebral body and at least a portion of the lower plate surface is configured to face the endplate of the second vertebral body;

ii. a center of the first opening is spaced from a first plane that both intersects the upper body surface and is normal to the vertical direction by a second distance along the vertical direction, and the center of the first opening is further spaced from a second plane that both intersects the lower body surface and is normal to the vertical direction a third distance along the vertical direction, such that the second and third distances are each less than the first maximum distance, the first plane spaced from the second plane by the first maximum distance; and iii. a center of the third opening is spaced from the first plane a fourth distance along the vertical direction and the center of the third opening is further spaced from the second plane a fifth distance along the vertical direction, such that the fourth and fifth distances are each less than the first maximum distance; and iv: the first recess is aligned with one of the first and second plate holes and the second recess is aligned with the other of the first and second plate holes.

2. The intervertebral implant of claim 1, wherein the body defines a first side surface and a second side surface spaced from the first side surface along a lateral direction that is perpendicular to both the forward and vertical directions, and the body further defines a first portion of the upper body surface that is continuous along the lateral direction from the first side surface to the second side surface.

3. The intervertebral implant of claim 2, wherein when the plate is mounted to the body both the center of the first opening and the center of the third opening are positioned between the first and second side surfaces with respect to the lateral direction.

4. The intervertebral implant of claim 2, wherein the body defines first and second walls that extend between the front body surface and the rear body surface, such that the body defines a first chamber disposed between the first side surface and the first wall, a second chamber disposed between the first wall and the second wall, and a third chamber disposed between the second wall and the second side surface.

5. The intervertebral implant of claim 1, wherein the plate further defines a plate recess disposed between the first and second plate holes, and the intervertebral implant further comprises a securing member configured to be received in the plate recess, such that when the plate is mounted to the body, the securing member at least partially covers both the first opening and the third opening.

6. The intervertebral implant of claim 5, further comprising the first bone fixation element and the second bone fixation element, wherein when: 1) the plate is mounted to the body; 2) the first bone fixation element is inserted into the first plate hole; and 3) the second bone fixation element is inserted into the second plate hole, the securing member is configured to be received in the plate recess such that the securing member at least partially covers both the first and second bone fixation elements to inhibit the first and second bone fixation elements from backing out of the respective first and second plate holes.

7. The intervertebral implant of claim 5, wherein the securing member defines a securing member hole configured to receive a fastener that connects the securing member to the plate.

8. The intervertebral implant of claim 5, wherein the securing member comprises inner threads around the securing member hole that are configured to mate with threads of the fastener, such that the fastener connects the securing member to the plate.

9. The intervertebral implant of claim 5, wherein the plate recess extends into the front plate surface toward the rear plate surface.

10. The intervertebral implant of claim 9, wherein the body further defines a first groove and a second groove, each of the first groove and the second groove extends along the vertical direction between the upper body surface and the lower body surface, each of the first and second grooves configured to receive a portion of the plate to mount the plate to the body.

11. The intervertebral implant of claim 10, wherein the plate comprises a first rail and a second rail, such that when the plate is mounted to the body, the first rail is disposed in the first groove and the second rail is disposed in the second groove.

12. The intervertebral implant of claim 5, wherein the plate further defines a third plate hole and a fourth plate hole that are configured to receive a third bone fixation element and a fourth bone fixation element, respectively, and the securing member further at least partially covers both the third and fourth plate holes when the securing member is received in the plate recess.

13. The intervertebral implant of claim 12, wherein the first and third plate holes are disposed closer to the upper body surface than the lower body surface, and the second and fourth plate holes are disposed closer to the lower body surface than the upper body surface.

14. The intervertebral implant of claim 13, wherein the first and third plate holes extend toward the upper body surface as they extend along an insertion direction from the front body surface to the rear body surface, and the second and fourth plate holes extend toward the lower body surface as they extend along the insertion direction.

15. The intervertebral implant of claim 12, further comprising the first bone fixation element, the second bone fixation element, the third bone fixation element, and the fourth bone fixation element.

16. The intervertebral implant of claim 15, wherein the first and third bone fixation elements extend above the upper body surface when they are driven into the first and third plate holes, respectively, and the second and fourth bone fixation elements extend below the lower body surface when they are driven into the second and fourth plate holes, respectively.

17. The intervertebral implant of claim 1, wherein the body further comprises teeth protruding from at least one of the upper body surface and the lower body surface.

18. The intervertebral implant of claim 1, further comprising the first bone fixation element.

19. The intervertebral implant of claim 18, wherein the first plate hole is located closer to the upper body surface than the lower body surface, such that the first bone fixation element is configured to be anchored to the first vertebral body.

20. The intervertebral implant of claim 19, further comprising the second bone fixation element.

21. The intervertebral implant of claim 20, wherein the second plate hole of the plate is located closer to the lower body surface than the upper body surface, such that the second bone fixation element is configured to be anchored to the second vertebral body.

22. The intervertebral implant of claim 21, wherein the first bone fixation element comprises a first head at least partially disposed in the first plate hole, and the second bone fixation element comprises a second head at least partially disposed in the second plate hole.

23. The intervertebral implant of claim 1, wherein the body is made of a first material, and the plate is made of a second material that is different from the first material.

24. The intervertebral implant of claim 23, wherein the first material comprises a biocompatible plastic.

25. The intervertebral implant of claim 24, wherein the second material comprises a metal.

26. The intervertebral implant of claim 1, wherein the plate is mounted to the body.

27. The intervertebral implant of claim 1, wherein when the plate is mounted to the body, an entirety of one of the first and third openings is: 1) spaced from the first plane by a distance measured along the vertical direction that is less than the first maximum distance; and 2) spaced from the second plane a distance measured along the vertical direction that is less than the first maximum distance.

28. The intervertebral implant of claim 27, wherein when the plate is mounted to the body, an entirety of the other of the first and third openings is: 1) spaced from the first plane a distance measured along the vertical direction that is less than the first maximum distance; and 2) spaced from the second plane a distance measured along the vertical direction that is less than the first maximum distance.

29. The intervertebral implant of claim 28, wherein the body defines a middle plane positioned equidistantly between the upper body surface and the lower body surface with respect to the vertical direction such that the middle plane does not intersect either the upper body surface or the lower body surface, and at least one of the first and third openings does not intersect the middle plane.

30. The intervertebral implant of claim 1, wherein when the plate is mounted to the body, the first and second plate holes are each positioned substantially between the first plane and the second plane.

31. The intervertebral implant of claim 1, wherein the body is an integral one-piece body.

\* \* \* \* \*